(12) United States Patent
Alvarez

(10) Patent No.: US 11,293,881 B2
(45) Date of Patent: Apr. 5, 2022

(54) MEASURING A WATER CUT OF HYDROCARBON FLUID IN A PRODUCTION PIPE

(71) Applicant: Saudi Arabian Oil Company, Dhahran (SA)

(72) Inventor: Jose Oliverio Alvarez, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 145 days.

(21) Appl. No.: 16/400,631

(22) Filed: May 1, 2019

(65) Prior Publication Data

US 2019/0257772 A1    Aug. 22, 2019

Related U.S. Application Data

(63) Continuation of application No. 16/191,071, filed on Nov. 14, 2018, now Pat. No. 10,466,182.

(60) Provisional application No. 62/585,965, filed on Nov. 14, 2017.

(51) Int. Cl.
*G01N 22/04* (2006.01)
*G01N 33/28* (2006.01)

(52) U.S. Cl.
CPC ......... *G01N 22/04* (2013.01); *G01N 33/2823* (2013.01); *G01N 33/2847* (2013.01)

(58) Field of Classification Search
CPC . G01N 22/04; G01N 33/2847; G01N 33/2823
USPC ........................................................ 342/22
See application file for complete search history.

(56) References Cited

U.S. PATENT DOCUMENTS

| 3,498,112 A | * | 3/1970 | Howard | G01N 22/04 |
| | | | | 73/61.48 |
| 3,681,684 A | | 8/1972 | Busker et al. | |
| 3,815,019 A | | 6/1974 | Wiles | |
| 4,423,623 A | * | 1/1984 | Ho | G01N 22/00 |
| | | | | 324/178 |

(Continued)

FOREIGN PATENT DOCUMENTS

| EP | 0637377 B1 | * | 11/1997 | ............. | G01N 22/04 |
| EP | 1451562 B1 | * | 9/2004 | ............... | G01F 1/74 |

(Continued)

OTHER PUBLICATIONS

International Search Report and Written Opinion issued in International Application No. PCT/US2018/060600 dated Mar. 8, 2019, 14 pages.

(Continued)

*Primary Examiner* — Bernarr E Gregory
*Assistant Examiner* — Nuzhat Pervin
(74) *Attorney, Agent, or Firm* — Fish & Richardson P.C.

(57) ABSTRACT

The present disclosure describes methods and systems, including computer-implemented methods, computer program products, and computer systems, for measuring a water cut for hydrocarbon fluid in a production pipe. One method includes transmitting a microwave through a first waveguide attached to a production pipe, wherein the microwave is directed to the hydrocarbon fluid in the production pipe; and obtaining, measurement results based on reflection or propagation of the microwave, wherein the measurement results are used to determine a water cut of the hydrocarbon fluid.

12 Claims, 7 Drawing Sheets

(56) References Cited

U.S. PATENT DOCUMENTS

| | | | | |
|---|---|---|---|---|
| 5,014,010 A * | 5/1991 | Helms | E21B 47/107 | 324/640 |
| 5,331,284 A * | 7/1994 | Jean | G01N 22/04 | 324/636 |
| 5,351,521 A * | 10/1994 | Cracknell | G01N 22/00 | 73/19.1 |
| 5,455,516 A * | 10/1995 | Jean | G01N 22/04 | 324/639 |
| 6,865,926 B2 * | 3/2005 | O'Brien | G01N 1/2202 | 73/23.27 |
| 7,345,622 B2 * | 3/2008 | Edvardsson | G01S 7/4056 | 342/124 |
| 7,621,171 B2 * | 11/2009 | O'Brien | G01N 1/2202 | 73/23.27 |
| 7,712,380 B2 * | 5/2010 | Xie | G01F 1/74 | 73/861.04 |
| 7,908,930 B2 * | 3/2011 | Xie | G01F 1/74 | 73/861.04 |
| 8,224,588 B2 * | 7/2012 | Wee | G01F 1/66 | 702/30 |
| 8,916,815 B2 | 12/2014 | Xie et al. | | |
| 8,986,922 B1 * | 3/2015 | Wach | G02B 5/285 | 430/321 |
| 9,528,780 B2 * | 12/2016 | Wray | G05D 23/192 | |
| 10,739,494 B2 * | 8/2020 | Thompson | E21B 49/00 | |
| 2004/0244501 A1 * | 12/2004 | Nyfors | G01F 1/74 | 73/861.63 |
| 2007/0085729 A1 * | 4/2007 | Edvardsson | H01Q 1/225 | 342/124 |
| 2007/0279073 A1 | 12/2007 | Wee | | |
| 2008/0295609 A1 * | 12/2008 | Xie | G01F 1/74 | 73/861.25 |
| 2008/0319685 A1 * | 12/2008 | Xie | G01F 1/712 | 702/45 |
| 2009/0088985 A1 * | 4/2009 | Wee | G01F 1/74 | 702/30 |
| 2010/0270291 A1 | 10/2010 | Kotzian et al. | | |
| 2013/0110411 A1 | 5/2013 | Black et al. | | |
| 2014/0090451 A1 * | 4/2014 | Surman | G01N 23/244 | 73/61.43 |
| 2015/0218941 A1 * | 8/2015 | Clarke | G01F 1/56 | 324/324 |
| 2016/0334343 A1 * | 11/2016 | Hurlimann | E21B 49/08 | |
| 2017/0191977 A1 * | 7/2017 | Nyfors | G01N 33/28 | |
| 2017/0248530 A1 | 8/2017 | Parker et al. | | |
| 2019/0047865 A1 * | 2/2019 | Zeller | B01J 19/129 | |

FOREIGN PATENT DOCUMENTS

| | | | | |
|---|---|---|---|---|
| EP | 1926991 B1 * | 4/2014 | | G01F 1/44 |
| GB | 2110377 | 6/1983 | | |
| GB | 2110377 A * | 6/1983 | | G01N 22/04 |
| GB | 2430493 A * | 3/2007 | | G01F 1/44 |
| WO | WO-2007043950 A2 * | 4/2007 | | G01F 23/284 |
| WO | WO-2007129901 A * | 11/2007 | | G01F 1/66 |
| WO | WO-2014027322 A2 * | 2/2014 | | H01Q 15/0086 |

OTHER PUBLICATIONS

Karimi et al., "Design and Dynamic Characterization of an Orientation Insensitive Microwave Water-Cut Sensor" IEEE Microwave Theory and Technique, Jun. 12, 2017, vol. 66, Issue 1, Jan. 2018, 10 pages.

GCC Examination Report in Gulf Cooperation Council Appln. No. GC 2018-36459, dated May 19, 2021, 4 pages.

* cited by examiner

MEASURING A WATER CUT OF HYDROCARBON FLUID IN A PRODUCTION PIPE

CROSS-REFERENCE TO RELATED APPLICATION(S)

This application is a continuation of and claims the benefit of priority to U.S. patent application Ser. No. 16/191,071, filed Nov. 14, 2018, which claims the benefit of U.S. Provisional Application No. 62/585,965, filed on Nov. 14, 2017, the contents of which are hereby incorporated by reference.

TECHNICAL FIELD

This disclosure relates to measuring a water cut of hydrocarbon fluid in a production pipe.

BACKGROUND

In an oil and gas production operation, hydrocarbon fluid is produced with multiphase flows. These flows can include oil, gas, and water. The amount of water in the produced fluid can be referred to as the water cut of the fluid. The water cut of the produced fluid is closely monitored to determine operational parameters such as oil/water contact level and water breakthrough. Accurate measurement of the water cut is thus important to the oil and gas production operation. The water cut measurement can also be referred to as on-line water determination.

SUMMARY

The present disclosure describes methods and systems, including computer-implemented methods, computer program products, and computer systems, for measuring a water cut of hydrocarbon fluid in a production pipe. One method for measuring a water cut of hydrocarbon fluid in a production pipe includes: transmitting a microwave through a first waveguide attached to a production pipe, wherein the microwave is directed to the hydrocarbon fluid in the production pipe; and obtaining, measurement results based on reflection or propagation of the microwave, wherein the measurement results are used to determine a water cut of the hydrocarbon fluid.

The foregoing and other implementations can each, optionally, include one or more of the following features, alone or in combination:

A first aspect, combinable with the general implementation, wherein the first waveguide uses a first filling material further comprising: determining that the water cut is within a particular water cut range; in response to determining that the water cut is within a particular water cut range, replacing the first waveguide with a second waveguide, wherein the second waveguide uses a second filling material that is different than the first filling material; transmitting a second microwave through the second waveguide; and obtaining second measurement results based on the second microwave.

A second aspect, combinable with any of the previous aspects, wherein the first filling material comprises quartz.

A third aspect, combinable with any of the previous aspects, wherein the second filling material comprises sapphire.

A fourth aspect, combinable with any of the previous aspects, wherein the first waveguide has a size that is substantially similar to a size of the production pipe.

A fifth aspect, combinable with any of the previous aspects, wherein the measurement results comprise magnitudes and phases of S parameters. Equivalently, The measurements can be in the time domain, for example travel time of the signal, losses in magnitude and dispersion.

Other implementations of this aspect include corresponding computer systems, apparatuses, and computer programs recorded on one or more computer storage devices, each configured to perform the actions of the methods. A system of one or more computers can be configured to perform particular operations or actions by virtue of having software, firmware, hardware, or a combination of software, firmware, or hardware installed on the system that, in operation, cause the system to perform the actions. One or more computer programs can be configured to perform particular operations or actions by virtue of including instructions that, when executed by data processing apparatus, cause the apparatus to perform the actions.

The details of one or more implementations of the subject matter of this specification are set forth in the accompanying drawings and the subsequent description. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

The following description is presented to enable any person skilled in the art to make and use the disclosed subject matter, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

This disclosure generally describes methods and systems, including computer-implemented methods, computer program products, and computer systems, for measuring the water cut of hydrocarbon fluid in a production pipe. In some operations, coaxial probes can be inserted on the wall of the production pipe to measure the water cut. However, the coaxial probe offers little penetration into the fluid, and thus may not obtain accurate measurement.

In some cases, waveguides can be used to direct microwaves to the hydrocarbon fluid in the production pipe. The microwave can propagate through the hydrocarbon fluid or be reflected from the hydrocarbon fluid. These propagated or reflected microwaves can be measured to determine the current water cut of the hydrocarbon fluid. In some implementations, the diameter of the waveguides can be determined based on the diameter of the production pipe. In addition, different waveguides having different shapes and filling materials can be used. Each of the different filling material can have electrical properties can produce accurate measurements in a particular range of water cut. FIGS. 1-7 and associated descriptions provide additional details of these implementations.

Figure 1:
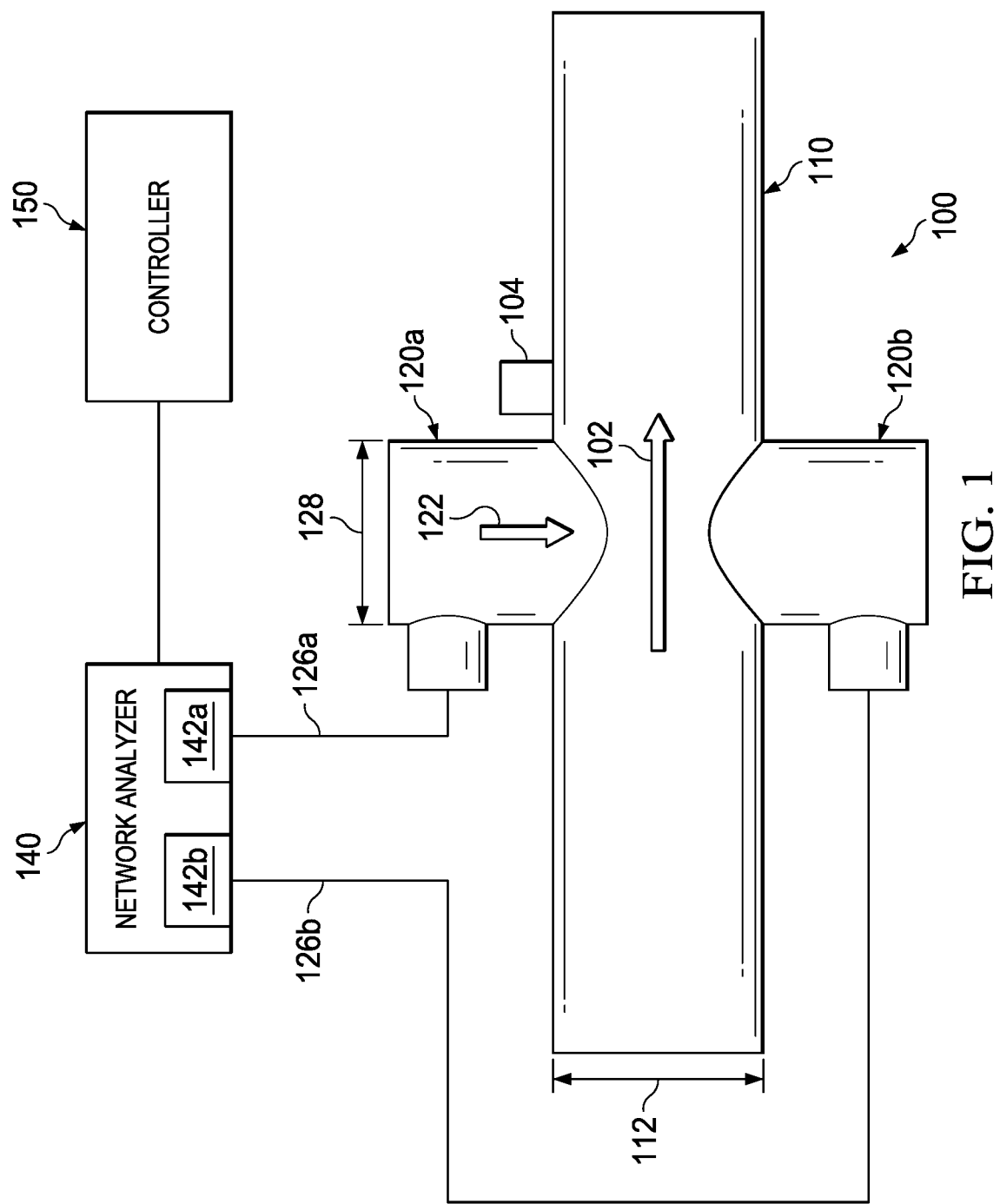
FIG. 1 is a schematic diagram that illustrates an example water cut measurement system, according to an implementation.

FIG. 1 is a schematic diagram that illustrates an example water cut measurement system 100, according to an implementation. The example system 100 includes waveguides 120a and 120b that are attached to a production pipe 110. A network analyzer 140 is connected with the waveguides 120a and 120b. The network analyzer 140 is communicatively coupled with a controller 150.

In the oil and gas industry, a production pipe, for example the production pipe 110, refers to a pipe that transports hydrocarbon fluid. In some implementations, the production pipe 110 can be constructed using carbon steel grade. In some cases, the production pipe 110 can be used to transport hydrocarbon fluid that is extracted by a wellbore drilling system to a storage tank at the drilling site. The production pipe 110 can also be used to transport hydrocarbon fluid between other endpoints in a hydrocarbon producing system, either on site or off site. In the illustrated example, the production pipe 110 transports hydrocarbon fluid 102. In some cases, the hydrocarbon fluid 102 represents fluid that is produced from a well system in the field. In these cases, the hydrocarbon fluid can also be referred to as production fluid. The hydrocarbon fluid 102 can include a mixture of oil, gas, water, or any combinations thereof. As illustrated, the production pipe 110 has a diameter 112.

Electromagnetically, materials such as fluid mixtures are characterized by two parameters: the permittivity and the magnetic permeability. For most materials, including downhole fluid mixtures in the production pipe 110, the magnetic permeability remains constant, while the permittivity varies as a function of frequency, temperature, and concentration of a particular component. The permittivity can be represented as a complex value, where the real part of the complex value is related to the capacitive properties of the material, and the imaginary part of the complex value is related to different loss mechanisms in the material.

The network analyzer 140 is a network analyzer that is configured to measure the magnitude and phase of the S parameters of an electrical network. The network analyzer 140 can also perform system error correction on the measurement results. In some implementations, the network analyzer 140 can be a vector network analyzer (VNA). The S parameters, also referred to as the scattering parameters or the s-parameters, describe the electrical behavior of linear electrical networks when undergoing various steady state stimuli by electrical signals. The permittivity of a material can be measured by sending electromagnetic waves through it and computing the S parameters. In the illustrated example, the network analyzer 140 can measure the magnitudes and the phase of the S parameter through reflections and propagations of microwaves. In some implementations, the network analyzer 140 can include one or more sets of transmitters and receivers. Each transmitter and receiver can include amplifiers, filters, and other electronic components that are configured to transmit or receive electronic signals.

Figure 4:
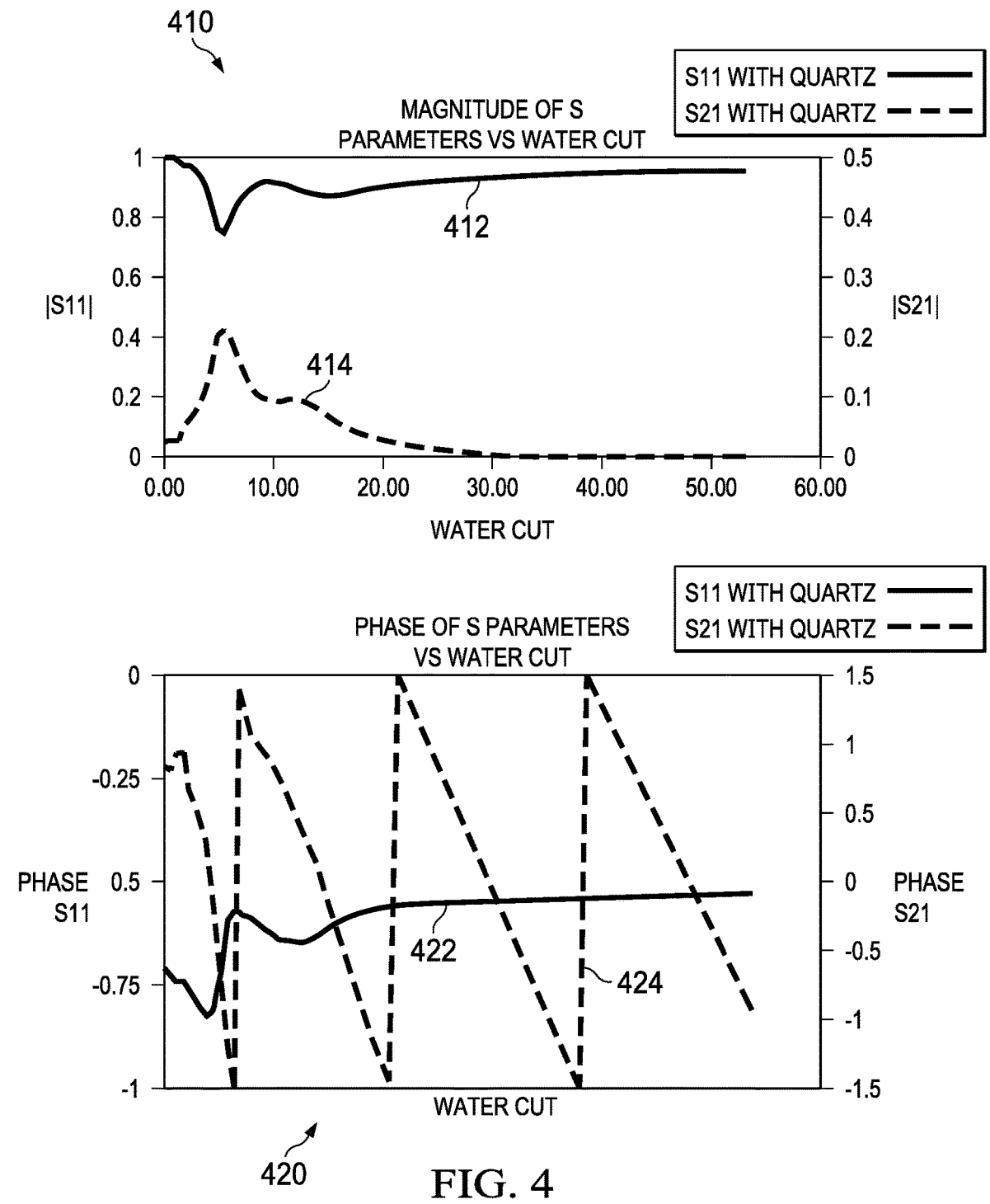
FIG. 4 illustrates example measurement results using quartz as the filling material of the waveguides, according to an implementation.
Figure 5:
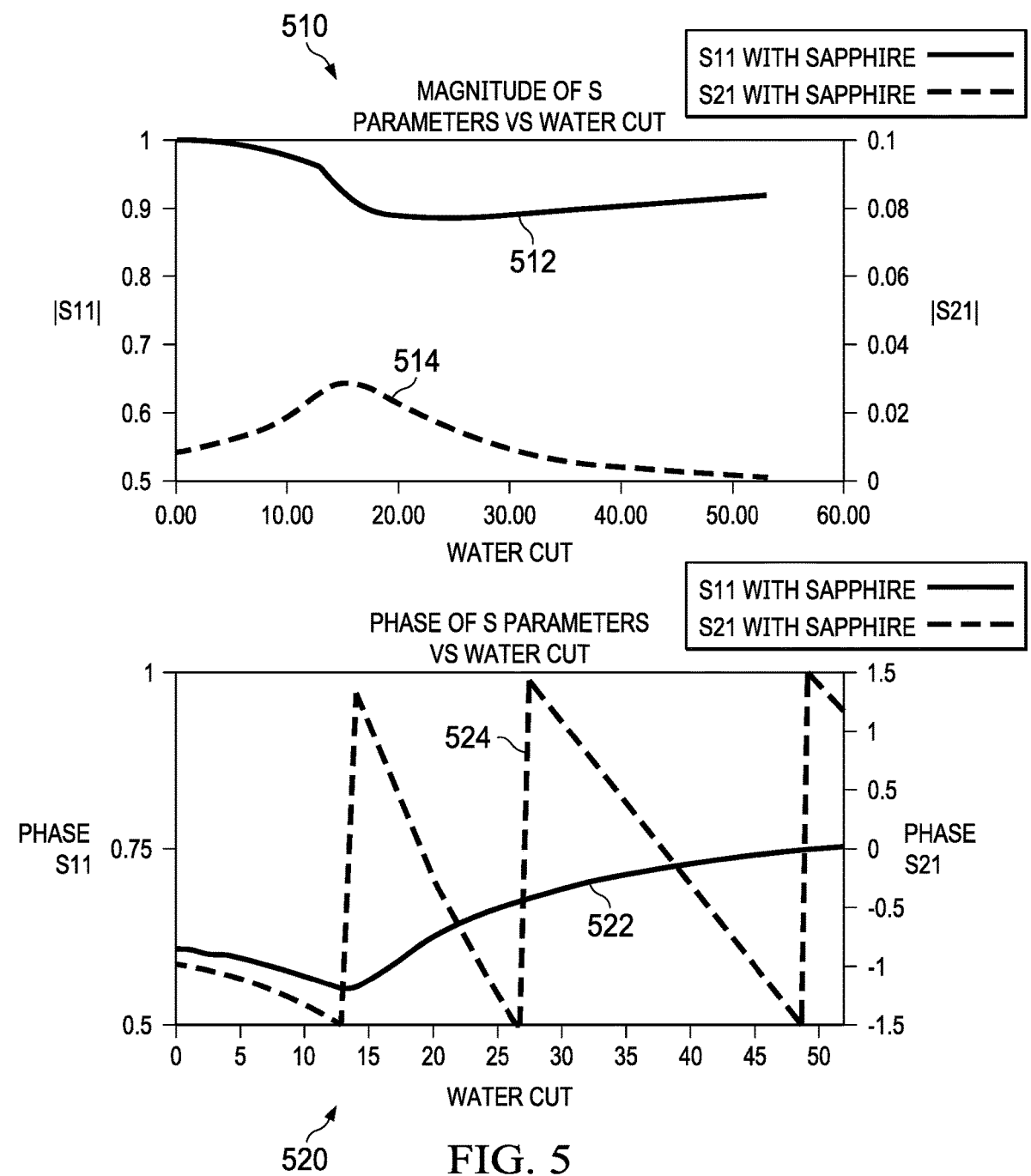
FIG. 5 illustrates example measurement results using sapphire as the filling material of the waveguides, according to an implementation.
Figure 6:
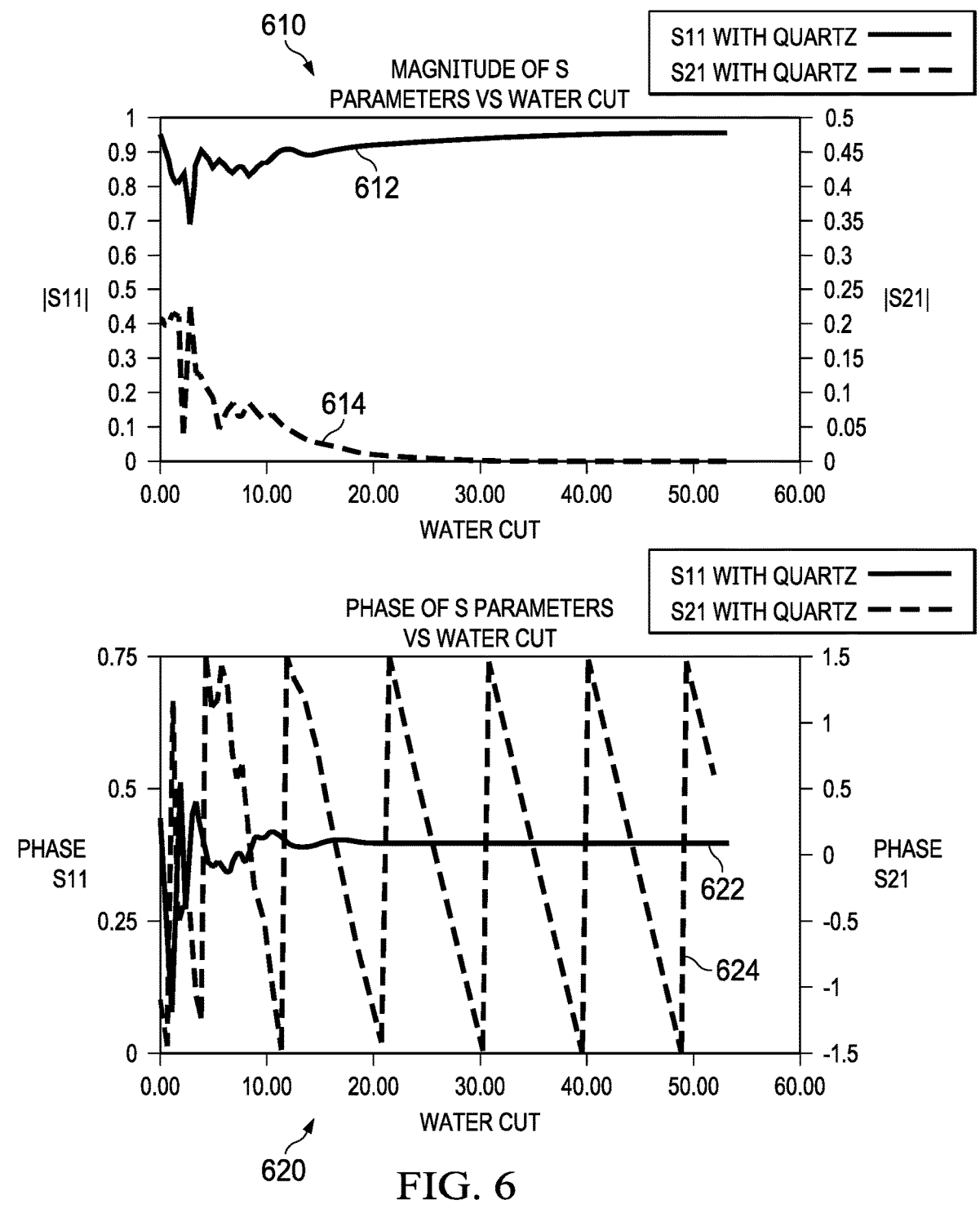
FIG. 6 illustrates example measurement results using waveguides having a different diameter, according to an implementation

The network analyzer 140 includes ports 142a and 142b. Each of the ports 142a and 142b can be used as interface to connect to the electronic network to be measured. In the illustrated example, a cable 126a connects the waveguide 120a to the port 142a; and a cable 126b connects the waveguide 120b to the port 142b. The cable 126a and 126b can be coaxial cables, fiber optical cables, or other media that can be used to transmit microwaves. In an example operation, the network analyzer 140 can generate electronic signals. The electronic signals are electromagnetic waves having amplitudes and phases. In one example, the electromagnetic waves can be microwaves, having frequencies between 300 MegaHertz (MHz) and 300 GigaHertz (GHz). The electromagnetic waves can be transmitted from the port 142a, and propagate over the cable 126a to reach the waveguide 120a. In the illustrated example, the electromagnetic wave is referred to as microwave 122. In some cases, the microwave 122 can further propagate to the waveguide 120b over the hydrocarbon fluid 102. The propagated signal can be received at the port 142b through the cable 126b. Alternatively or additionally, the microwave 122 can reflect from the hydrocarbon fluid 102 and the reflected signal can be received at the port 142a over the cable 126a. The S parameters measurements of the propagated signal and the reflected signal can be used to determine the permittivity of the hydrocarbon fluid 102, and thus the water cut of the hydrocarbon fluid 102. FIGS. 4-6 and associated descriptions provide additional details of these implementations.

The waveguides 120a and 120b have a diameter 128. In some implementations, the diameter 128 of the waveguides 120a and 120b are substantially similar to the diameter 112 of the production pipe 110. In some implementations, the diameter of the production pipe 110 can be chosen based on the cutoff frequencies of different propagating modes.

In a pipe such as the production pipe 110, there are two kinds of propagating modes or traverse modes for electromagnetic waves to propagate through: the transverse electric (TE) and transverse magnetic (TM) modes. In a TE mode, there is a magnetic field along the direction of propagation but there is no electric field in the direction of propagation. In a TM mode, there is an electric field along the direction of propagation but there is no Magnetic field in the direction of propagation. The propagation of the electromagnetic waves in the pipe can be characterized by the Maxwell's equations, which yield multiple solutions. Each solution can be represented as a propagation sub mode, denoted as $TE_{11}$, $TE_{12}$, $TM_{01}$, $TM_{11}$. The cutoff frequency for a particular mode or sub mode represents the frequency below which there is no propagation of that particular mode or sub mode. For the sub modes in the TM mode, $TM_{01}$ has the lowest cutoff frequency. For the sub modes in the TE mode, $TE_{11}$ has the lowest cutoff frequency.

Figure 3:
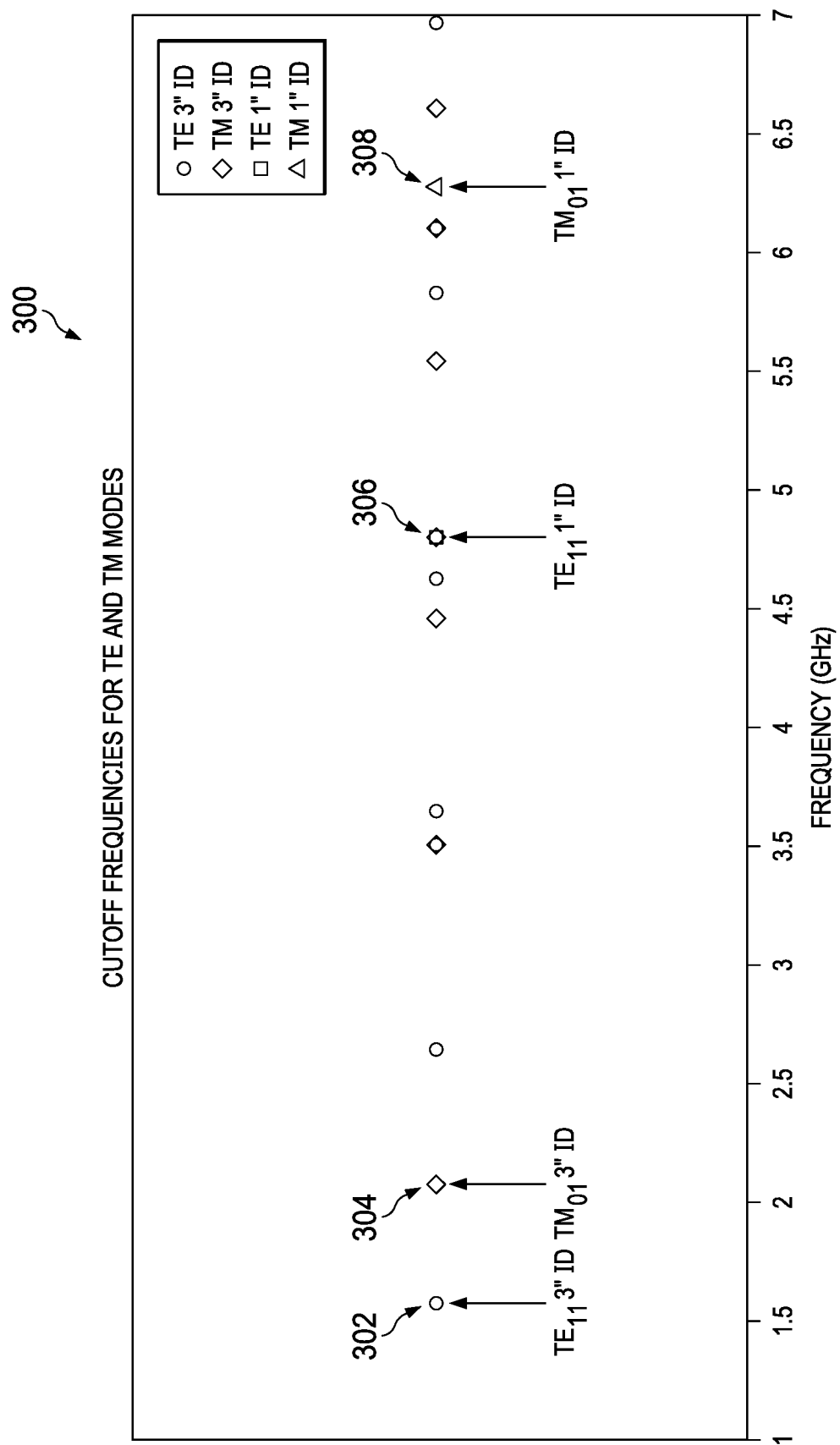
FIG. 3 is a chart illustrating example cutoff frequencies for waveguides of different diameters, according to an implementation.

FIG. 3 is a chart 300 illustrating example cutoff frequencies for waveguides of different diameters, according to an implementation. In the illustrated example, the production pipe has a 3-inch diameter, and the waveguides have 3-inch diameters and 1-inc diameters. In the chart 300, point 302 represent the cutoff frequency of the $TE_{11}$ sub mode for waveguides having a 3-inch diameter. Point 304 represents the cutoff frequency of the $TM_{01}$ mode for waveguides having a 3-inch diameter. Points 306 and 308 represent the cutoff frequencies of the $TE_{11}$ mode and $TM_{01}$ modes for waveguides having a 1-inch diameter. As illustrated, if waveguides having a 3-inch diameter is used to propagate microwaves through a pipe with similar size, for example having a 3-inch diameter, the cutoff frequencies of the $TM_{01}$ and $TE_{11}$ sub modes are the lowest cutoff frequencies, as represented by the points 302 and 304, respectively. In other words, no other propagation sub modes would be present to generate interfering measurements. On the other hand, for waveguides that are much smaller than the pipe, for example, for waveguides having a 1-inch diameter, there are many other sub modes that may have cutoff frequencies that are lower than the cutoff frequencies represented by the points 306 and 308, as represented by different points on the left of the points 306, which would produce interfering measurement results. Therefore, using waveguides having a substantially similar diameter, for example within 10%, as the production pipe that transport the hydrocarbon fluid can provide a better measurement result. In some cases, the waveguides may use different shapes, for example having a rectangular cross section instead of a circular cross section. The rectangular cross section can have a length and a width, with length larger than the width. In these or other cases, instead of the diameter, the size of the waveguides can be represented by the length of the rectangular cross section. In these cases, waveguides having the size that is substantially similar to the size of the pipe can be used.

In some cases, the size of the waveguides can be chosen based on the cutoff frequencies for the $TE_{11}$ sub mode and the $TM_{01}$ sub mode. For example, the size of the waveguides can be determined so that the cutoff frequency for the $TE_{11}$ sub mode is higher than the cutoff frequency for the $TM_{01}$ mode for that particular size of the waveguides.

The waveguides 120a and 120b represent waveguides that are configured to guide microwave 122 through the hydrocarbon fluid 102 that flows inside the production pipe 110. In some implementations, a pair of waveguides 120a-b having the same size and filling materials are used to measure propagating microwaves. Alternatively or additionally, one waveguide, for example, the waveguide 120a or 120b, can be used to measure reflected microwaves. In the illustrated example, the waveguides 120a and 120b are attached to opposite sides of the production pipe 110 and thus can form a transmitter-receiver pair. The pair of waveguides 120a-b are positioned in a vertical alignment so that microwave can propagate from one waveguide to the other. In one example operation, the waveguide 120a directs the microwave 122 to propagation in a downward direction, through the hydrocarbon fluid 102, to the waveguide 120b. The waveguides 120a and 120b can be attached to the production pipe 110 by welding, flanges, threadolets, or any other installation techniques.

Returning to FIG. 1, in some implementations, the filling materials of the waveguides 120a and 120b can be chosen based on the amount of water in the hydrocarbon fluid 102 and in the production pipe 110. In some cases, filling materials having low varying permittivity and low losses (low imaginary part of the permittivity) for a wide range of temperatures can be used. These materials can reduce the uncertainty introduced by the temperature effect. Examples of the filling materials include quartz, sapphire, zirconia, rutile, diamond and titanium dioxide. Alternatively, materials having well-known electrical properties, such as ceramic derived materials or casting resin materials, can be used.

FIG. 4 illustrates example measurement results using quartz as the filling material of the waveguides, according to an implementation. FIG. 4 includes charts 410 and 420, illustrating the magnitude and phase of the S parameter for different water cuts (obtained by mixing different percentages of oil and water), respectively. In some implementations, the S parameter can be measured based on the microwave that propagate from one waveguide to the other waveguide across the pipe. Such measurement results can be denoted as S21, as shown by curves 414 and 424. The S parameter can also be measured based on the microwave that is reflected from the same waveguide. Such measurement results can be denoted as S11, as shown by curves 412 and 422. The x-axis of both charts 410 and 420 denote water cut of the hydrocarbon fluid to be measured. The left and right y-axis of the chart 410 denote the ratio with respect to the signal transmitted from the vector network analyzer of the S11 and S21 measurement, respectively. The left and right y-axis of the chart 420 denote the phase in radian units of the S11 and S21 measurement, respectively. In some implementations, the field measurement results can be lower than the number shown in FIG. 4 due to losses in propagations.

As illustrated in the chart 410, the peak of the curves 412 and 414 are obtained at about 5% water cut. The magnitude of the S parameter from the S21 measurement increases as the water cut increases before the water cut reaches the peak, and decreases as the water cut increases after the water cut reaches the peak. Therefore, if we obtain a particular magnitude measurement of the S parameter, for example at 0.3 for S21 measurement, we may have two possible water cut values that can match to this measurement result, for example, 0.03 and 0.07. However, the phase measurement for these two water cuts are different, as shown in the chart 420. Therefore, by obtaining both the magnitude and the phase of the S parameter, the water cut of the hydrocarbon fluid can be determined. In some implementations, the S parameters for water cut can be obtained based on lab measurement (reference/calibration, measured by other devices such as a separator), numerically obtained data (simulation), and a combination thereof. In some implementations, the water cut can be determined based on either the S11 measurement or S21 measurement. Alternatively, or additionally, both S11 and S21 measurements can be conducted, and their results can be analyzed together to obtain a more accurate result. Furthermore, similar measurement can be performed in time domain by using signal generators and signal analyzers.

As shown in the chart 410, the measured magnitude of the S parameter using waveguides having quartz as the filling material are relatively flat after water cut reaches beyond about 15%. In other words, the measurement results are less sensitive to the changing of water cut after about 15%. Therefore, in the range where the water cut is beyond 15%, noise in the measurement data may become a significant factor and make the measurement less accurate.

FIG. 5 illustrates example measurement results using sapphire as the filling material of the waveguides, according to an implementation. FIG. 5 includes charts 510 and 520, illustrating the magnitude and phase of the S parameter for different water cut, respectively. In FIG. 5, curves 512 and 522 represent the measurement results obtained based on reflection; and curves 514 and 524 represent the measurement results obtained based on propagation.

As illustrated in the chart 510, the peaks of the curves 512 and 514 are obtained at about 15% water cut. The slope of the curves 512 and 514 are relatively steep between about 15% to about 45% water cut. Therefore, waveguides filled with sapphire can provide better measurement results than waveguides filled with quartz for water cut within this range.

As discussed previously, the measurement results of the S parameter vary based on diameters of the production pipe and the waveguides. The measurement results in FIG. 4 and FIG. 5 are obtained based on the production pipe having a diameter of 76.2 millimeter (mm) and the waveguides having a diameter of 62 mm. FIG. 6 illustrates example measurement results using waveguides having a diameter of 20 mm, according to an implementation. FIG. 6 includes charts 610 and 620, illustrating the magnitude and phase of the S parameter for different water cut, respectively. In FIG. 6, curves 612 and 622 represent the measurement results obtained based on reflection; and curves 614 and 624 represent the measurement results obtained based on propagation. As illustrated in FIG. 6, because the waveguides have a diameter that is much smaller than the pipe, the magnitude curves have many local maxima and minima, which makes it difficult to determine the water cut based on the measurement.

Returning to FIG. 1, the system 100 also includes the controller 150. The controller 150 represents a computing device that is configured to determine water cut based on the measurement results obtained by the vector network analyzer 140. The controller 150 is connected with the vector network analyzer 140 using wireless technologies, wireline technologies, or a combination thereof. In some implementations, the controller 150 can store, or have access to the data of S parameter measurements for different water cuts. For example, the controller 150 can store the measurement data as shown in FIGS. 4-6. The controller 150 can receive the measurement results from the vector network analyzer 140, and determine the current water cut of the hydrocarbon fluid 102 by comparing the measurement results with the stored data (from measurement or numerical experiments). In some implementations, as illustrated, the controller 150 can be implemented on a different hardware platform as the vector network analyzer 140. Alternatively, the controller 150 can be implemented as a component of the vector network analyzer 140.

In some operations, the waveguides 120a and 120b can be replaced based on the current water cut of the hydrocarbon fluid 102. As discussed previously, waveguides with different filling materials can be suitable for different water cut ranges. Therefore, by monitoring the progression of the water cut of the hydrocarbon fluid 102, waveguides with different filling materials can be substituted if the water cut has passed a threshold. In one example, waveguides using quartz as filling material can be used in initial measurement. The controller 150 can monitor the current water cut of the hydrocarbon fluid 102. If the current water cut rises over 15%, the controller 150 can output an alert. Operational personnel can replace the waveguides having quartz as filling material with waveguides having sapphire as filling material. If the water cut passes another threshold, waveguides using different filling materials, for example, zirconia or titanium dioxide, can further replace the waveguides having sapphire as the filling material. This approach can provide accurate measurement for hydrocarbon fluid in different water cut ranges.

In some cases, the permittivity, and therefore the S parameters, can also be impacted by the temperature of the hydrocarbon fluid 102. In some implementations, the system 100 can include one or more temperature sensors 104 that are attached the production pipe 110 to measure the temperature of the hydrocarbon fluid 102. The measured temperature data can be transmitted to the controller 150 for analysis. The controller 150 can correct any bias of the measurement results based on the measured temperature. In some implementations, the temperature sensor 104 can be implemented as a component of the waveguides 120a and 120b.

Figure 2:
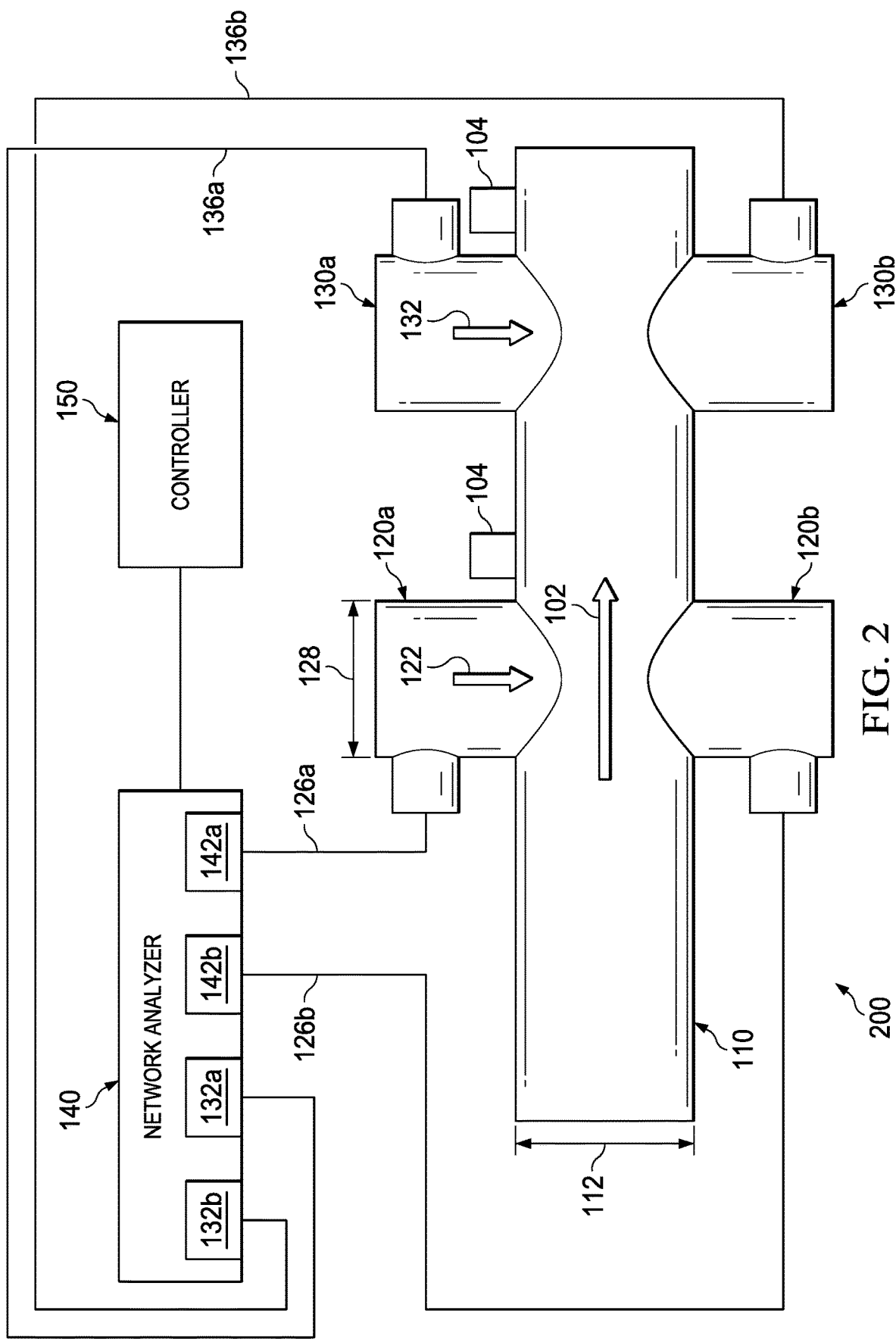
FIG. 2 is a schematic diagram that illustrates another example water cut measurement system, according to an implementation.

In some implementations, instead of replacing waveguides, waveguides having different filling materials can be attached to the production pipe. Measurement results obtained through different waveguides can be used to determine water cut in different ranges. FIG. 2 is a schematic diagram that illustrates another example water cut measurement system 200, according to an implementation. The example system 200 includes a second pair of waveguides 130a and 130b that are attached to the production pipe 110. The second pair of waveguides 130a and 130b are connected to ports 132a and 132b of the vector network analyzer 140 using cables 136a and 136b, respectively.

In some implementations, the waveguides 130a and 130b use filling materials that are selected for water cut measurement in a range that is different than the waveguides 120a and 120b. For example, the waveguides 120a and 120b can use quartz as the filling material and thus are suitable for measuring water cut between 0 to 15%, while the waveguides 130a and 130b can use sapphire as the filling material and thus are suitable for measuring water cut between 15 to 45%. In the initial measurement, the controller 150 determines the water cut of the hydrocarbon fluid 102 based on measurements obtained through the waveguides 120a and 120b. In one example operation, the controller 150 can transmit a command to the vector network analyzer 140 to transmit and receive electronic signals through the ports 142a and 142b. The controller 150 can determine the current water cut within a first water cut range, for example, between 0% and 15%. The controller 150 can continue to monitor the water cut. If the controller 150 determines that the current water cut is in a different water cut range, for example, between 15% and 45%, the controller 150 can determine the current water cut based on measurement results using the waveguides 130a and 130b. In one example, the controller 150 can transmit a command to the vector network analyzer 140 to stop transmitting and receiving electronic signals through the ports 142a and 142b. Instead, the controller 150 can instruct the vector network analyzer 140 to transmit and receive electronic signals through the ports 132a and 132b, which result in microwave 132 directed by the waveguides 130a and 130b. Accordingly, the controller 150 can determine the current water cut based on measurements obtained through the waveguides 130a and 130b. This approach can provide accurate measurement for different water cut regions without replacing the waveguides during the measurements.

In some cases, a production pipe can have different diameters at different locations. For example, the production pipe can include different segments that have different diameters. Waveguides having different diameters can be attached to different segments to match the diameter of the respective segment. These different waveguides can be connected to the same or different vector network analyzers. By obtaining the measurements through these different waveguides having different filling materials and sizes, the water cut of the hydrocarbon fluid in different segments of the production pipe can be determined.

Figure 7:
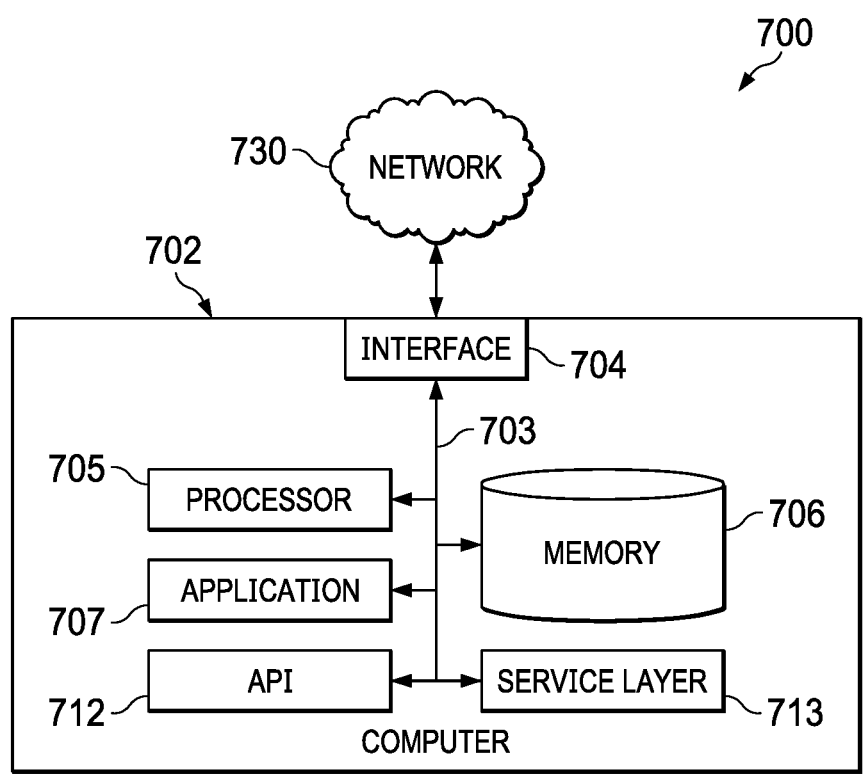
FIG. 7 is a high level architecture block diagram of a water cut measuring system, according to an implementation.

FIG. 7 is a high level architecture block diagram of a water cut measuring system 700 that measures water cut based on the methods described herein, according to an implementation. At a high level, the illustrated system 700 includes a water cut measuring computer 702 coupled with a network 730. The water cut measuring computer 702 can be used to implement the controller 150 discussed in FIGS. 1 and 2.

The described illustration is only one possible implementation of the described subject matter and is not intended to limit the disclosure to the single described implementation. Those of ordinary skill in the art will appreciate the fact that the described components can be connected, combined, and/or used in alternative ways, consistent with this disclosure.

The network 730 facilitates communication between the computer 702 and other components, for example, components that obtain observed data for a location and transmit the observed data to the computer 702. The network 730 can be a wireless or a wireline network. The network 730 can also be a memory pipe, a hardware connection, or any internal or external communication paths between the components.

The computer 702 includes a computing system configured to perform the method as described herein. In some cases, the algorithm of the method can be implemented in an executable computing code, for example, C/C++ or MAT-LAB executable codes. In some cases, the computer 702 can include a standalone Linux system that runs batch applications. In some cases, the computer 702 can include mobile or personal computers that have sufficient memory size to process each block of the geophysical data.

The computer 702 may comprise a computer that includes an input device, such as a keypad, keyboard, touch screen, microphone, speech recognition device, other devices that can accept user information, and/or an output device that conveys information associated with the operation of the computer 702, including digital data, visual and/or audio information, or a GUI.

The computer 702 can serve as a client, network component, a server, a database, or other persistency, and/or any other component of the system 700. In some implementations, one or more components of the computer 702 may be configured to operate within a cloud-computing-based environment.

At a high level, the computer 702 is an electronic computing device operable to receive, transmit, process, store, or manage data and information associated with the system 700. According to some implementations, the computer 702 may also include, or be communicably coupled with, an application server, e-mail server, web server, caching server, streaming data server, business intelligence (BI) server, and/or other servers.

The computer 702 can receive requests over network 730 from a client application (for example, executing on another computer 702) and respond to the received requests by processing said requests in an appropriate software application. In addition, requests may also be sent to the computer 702 from internal users (for example, from a command console or by another appropriate access method), external or third parties, other automated applications, as well as any other appropriate entities, individuals, systems, or computers.

Each of the components of the computer 702 can communicate using a system bus 703. In some implementations, any and/or all the components of the computer 702, both hardware and/or software, may interface with each other and/or the interface 704, over the system bus 703, using an application programming interface (API) 712 and/or a service layer 713. The API 712 may include specifications for routines, data structures, and object classes. The API 712 may be either computer language-independent or -dependent and refer to a complete interface, a single function, or even a set of APIs. The service layer 713 provides software services to the computer 702 and/or the system 700. The functionality of the computer 702 may be accessible for all service consumers using this service layer. Software services, such as those provided by the service layer 713, provide reusable, defined business functionalities, through a defined interface. For example, the interface may be software written in JAVA, C++, or other suitable languages providing data in Extensible Markup Language (XML) format or other suitable formats. While illustrated as an integrated component of the computer 702, alternative implementations may illustrate the API 712 and/or the service layer 713 as stand-alone components in relation to other components of the computer 702 and/or system 700. Moreover, any or all parts of the API 712 and/or the service layer 713 may be implemented as child or sub-modules of another software module, enterprise application, or hardware module, without departing from the scope of this disclosure.

The computer 702 includes an interface 704. Although illustrated as a single interface 704 in FIG. 7, two or more interfaces 704 may be used according to particular needs, desires, or particular implementations of the computer 702 and/or system 700. The interface 704 is used by the computer 702 for communicating with other systems in a distributed environment—including within the system 700—connected to the network 730 (whether illustrated or not). Generally, the interface 704 comprises logic encoded in software and/or hardware in a suitable combination and operable to communicate with the network 730. More specifically, the interface 704 may comprise software supporting one or more communication protocols associated with communications such that the network 730 or interface's hardware is operable to communicate physical signals within and outside of the illustrated system 700.

The computer 702 includes a processor 705. Although illustrated as a single processor 705 in FIG. 7, two or more processors may be used according to particular needs, desires, or particular implementations of the computer 702 and/or the system 700. Generally, the processor 705 executes instructions and manipulates data to perform the operations in the computer 702. Specifically, the processor 705 executes the functionality required for processing geophysical data.

The computer 702 also includes a memory 706 that holds data for the computer 702 and/or other components of the system 700. Although illustrated as a single memory 706 in FIG. 7, two or more memories may be used according to particular needs, desires, or particular implementations of the computer 702 and/or the system 700. While memory 706 is illustrated as an integral component of the computer 702, in alternative implementations, memory 706 can be external to the computer 702 and/or the system 700.

The application 707 is an algorithmic software engine providing functionality according to particular needs, desires, or particular implementations of the computer 702 and/or the system 700, particularly with respect to functionality required for processing geophysical data. For example, application 707 can serve as one or more components/applications described in FIGS. 1-6. Further, although illustrated as a single application 707, the application 707 may be implemented as multiple applications 707, on the computer 702. In addition, although illustrated as integral to the computer 702, in alternative implementations, the application 707 can be external to the computer 702 and/or the system 700.

There may be any number of computers 702 associated with, or external to, the system 700 and communicating over network 730. Further, the terms "client," "user," and other appropriate terminology may be used interchangeably, as appropriate, without departing from the scope of this disclosure. Moreover, this disclosure contemplates that many users may use one computer 702, or that one user may use multiple computers 702.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non-transitory computer-storage medium for execution by, or to control the operation of, data processing apparatus. Alternatively, or in addition, the program instructions can be encoded on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include, special purpose logic circuitry, for example, a central processing unit (CPU), a field programmable gate array (FPGA), or an application specific integrated circuit (ASIC). In some implementations, the data processing apparatus and/or special purpose logic circuitry may be hardware-based and/or software-based. The apparatus can optionally include code that creates an execution environment for computer programs, for example, code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS, or any other suitable conventional operating system.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components, as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline and/or wireless digital data communication, for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of the specification or on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking and parallel processing may be advantageous.

Moreover, the separation and/or integration of various system modules and components in the implementations described previously should not be understood as requiring such separation and/or integration in all implementations, and it should be understood that the described program components and systems can generally be integrated together in a single software product or packaged into multiple software products.

Accordingly, the previous description of example implementations does not define or constrain this disclosure. Other changes, substitutions, and alterations are also possible without departing from the spirit and scope of this disclosure.

The invention claimed is:

1. A method for measuring water cut in hydrocarbon fluid, comprising:
    attaching a first waveguide to a production pipe that transports hydrocarbon fluid extracted from a wellbore by a wellbore drilling system, wherein the first waveguide is filled with a first filling material;

transmitting a microwave through the first waveguide attached to the production pipe, wherein the microwave is directed to the hydrocarbon fluid in the production pipe;

obtaining first measurement results based on reflection or propagation of the microwave, wherein the first measurement results are used to determine a water cut of the hydrocarbon fluid;

determining that the water cut is within a particular water cut range;

in response to determining that the water cut is within a particular water cut range, replacing the first waveguide with a second waveguide, wherein the second waveguide is filled with a second filling material that is different than the first filling material;

transmitting a second microwave through the second waveguide, wherein the second microwave is directed to the hydrocarbon fluid in the production pipe; and obtaining second measurement results based on the second microwave, wherein the second measurement results are used to determine the water cut of the hydrocarbon fluid.

2. The method of claim 1, wherein the first filling material comprises quartz.

3. The method of claim 2, wherein the second filling material comprises sapphire.

4. The method of claim 1, wherein the first waveguide has a size that is substantially similar to a size of the production pipe.

5. The method of claim 1, wherein the measurement results comprise magnitudes and phases of S parameters.

6. The method of claim 1, wherein the measurement results comprise at least one of travel time, loss in magnitude, or a dispersion signal.

7. A water cut measuring system, comprising:
a first waveguide attached to a production pipe at a first location, wherein the first waveguide is configured to direct microwaves to hydrocarbon fluids in the production pipe, wherein the first waveguide is filled with a first filling material comprising electrical properties affecting transmission of the microwave to the hydrocarbon fluids;

a second waveguide attached to the production pipe at a second location upstream or downstream of the first location, wherein the second waveguide is configured to direct microwaves to the hydrocarbon fluids in the production pipe, wherein the second waveguide is filled with a second filling material that is different than the first filling material;

a network analyzer connected with the first waveguide and the second waveguide, wherein the network analyzer is configured to:
transmit microwaves to the first waveguide and the second waveguide;
receive microwaves reflected from the hydrocarbon fluid or propagated through the hydrocarbon fluids; and
obtain measurement results based on the reflected or propagated microwave, wherein the measurement results are used to determine a water cut of the hydrocarbon fluid; and a controller communicatively coupled with the network analyzer, wherein the controller comprises:
a memory; and
at least one hardware processor communicatively coupled with the memory and configured to determine a water cut of the hydrocarbon fluid based on the measurement results,
wherein the at least one hardware processor configured to determine that the water cut is within a particular water cut range; and
in response to determining that the water cut is within a particular water cut range, determine a second water cut of the hydrocarbon fluid using the second waveguide.

8. The water cut measuring system of claim 7, wherein the first filling material comprises quartz.

9. The water cut measuring system of claim 8, wherein the second filling material comprises sapphire.

10. The water cut measuring system of claim 7, wherein the first waveguide has a size that is substantially similar to a size of the production pipe.

11. The water cut measuring system of claim 7, wherein the measurement results comprise magnitudes and phases of S parameters.

12. The water cut measuring system of claim 7, wherein the measurement results comprise at least one of travel time, loss in magnitude, or a dispersion signal.

* * * * *